(12) United States Patent
Wolowacz et al.

(10) Patent No.: US 6,946,003 B1
(45) Date of Patent: Sep. 20, 2005

(54) IMPLANTS FOR CONNECTIVE TISSUE RECONSTRUCTION

(75) Inventors: Sorrel Wolowacz, High Peak (GB); Nicholas John Cotton, Westborough, MA (US)

(73) Assignee: Smith & Nephew plc, London (GB)

(*) Notice: Subject to any disclaimer, the term of this patent is extended or adjusted under 35 U.S.C. 154(b) by 0 days.

(21) Appl. No.: 09/979,786

(22) PCT Filed: May 22, 2000

(86) PCT No.: PCT/GB00/01933
§ 371 (c)(1),
(2), (4) Date: Mar. 18, 2002

(87) PCT Pub. No.: WO00/72782
PCT Pub. Date: Dec. 7, 2000

(30) Foreign Application Priority Data
May 27, 1999 (GB) .................................. 9912240

(51) Int. Cl.[7] .............................................. A61F 2/02
(52) U.S. Cl. ................................ 623/23.72; 623/902
(58) Field of Search ...................... 623/23.72, 13.19, 623/13.2, 13.11, 23.73–23.76, 902; 606/151

(56) References Cited

U.S. PATENT DOCUMENTS

| | | | | |
|---|---|---|---|---|
| 955,541 | A | * | 4/1910 | Petersen .................. 139/387 R |
| 4,816,028 | A | * | 3/1989 | Kapadia et al. ............ 623/1.52 |
| 4,834,755 | A | * | 5/1989 | Silvestrini et al. ........ 623/13.19 |
| 4,894,063 | A | * | 1/1990 | Nashef ..................... 623/13.17 |
| 4,917,700 | A | * | 4/1990 | Aikins ...................... 623/13.19 |
| 4,946,377 | A | * | 8/1990 | Kovach .................... 623/13.18 |
| 5,108,433 | A | * | 4/1992 | May et al. ..................... 606/72 |
| 5,134,006 | A | * | 7/1992 | Irvin ............................ 428/68 |
| 5,176,708 | A | * | 1/1993 | Frey et al. ................. 623/13.2 |
| 6,027,744 | A | * | 2/2000 | Vacanti et al. .............. 424/426 |

* cited by examiner

Primary Examiner—Alvin J. Stewart
(74) Attorney, Agent, or Firm—Stites & Harbison PLLC; Douglas E. Jackson

(57) ABSTRACT

Biocompatible, implantable material comprising flexible, elongate tape and a plurality of elongate elements, each elongate element being aligned along and independently translatable in the longitudinal direction of the tape; implants manufactured from this material, for the partial or total replacement or reinforcement of connective tissue such as ligament, cartilage, bone, meniscus tendon, skin.

40 Claims, 6 Drawing Sheets

Fig.3
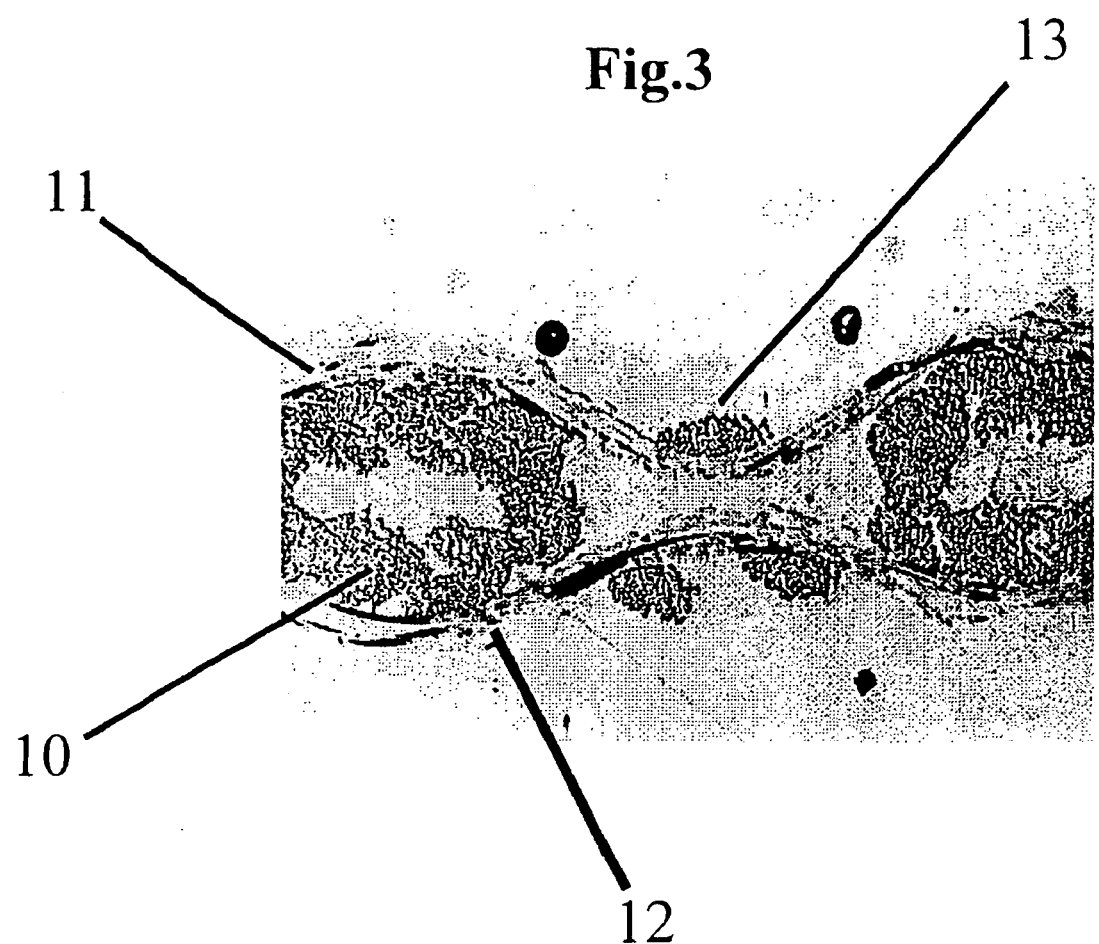
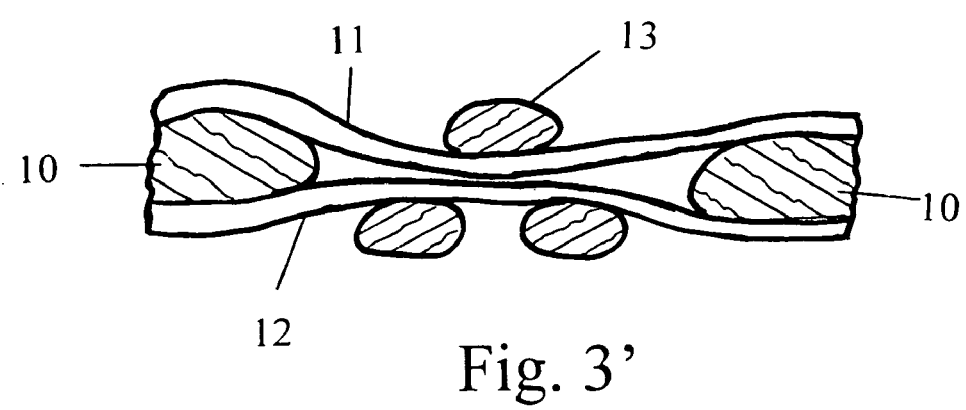
Fig. 3'

IMPLANTS FOR CONNECTIVE TISSUE RECONSTRUCTION

The present invention relates to a biocompatible, implantable material, to implants manufactured therefrom, for the partial or total replacement or reinforcement of connective tissue such as ligament, cartilage, bone, meniscus, tendon, skin and the like, and to methods for the total or partial replacement of connective tissue in a mammalian patient comprising the step of implanting the implants according to the invention.

Surgical treatments for injured ligaments such as cruciate ligaments fall generally into two main groups. These are tissue grafting on the one hand and replacement by a synthetic device on the other.

Ligament reconstruction with autograft tissue is the most common treatment, but donor site morbidity, the paucity of tissue available for grafting and necrosis of the graft following implantation, resulting in poor graft strength, remain a problem. The use of allogenic or xenogenic donor tissue represents an alternative to the use of autograft and has the advantage that it eliminates the problems associated with the tissue harvesting procedure. On the other hand, the perceived risk of disease transmission and immunogenic responses to the graft has limited their use to a small fraction of ligament reconstructions.

Turning to the matter of synthetic implants, devices (see U.S. Pat. No. 4,668,233, U.S. Pat. No. 4,775,380 and EP 0 223 370) have been proposed which are intended to encourage the invasion of tissue on implantation, in the hope that the tissue ingrowth will contribute to the mechanical strength and longevity of the device.

It has also been proposed to combine permanent devices of the type described above with a material which can be re-absorbed by the body (i.e. a resorbable material) to promote the ingrowth of tissue. U.S. Pat. No. 4,127,902 and U.S. Pat. No. 3,971,670 describe structures consisting of a combination of a load absorbing component of a non-resorbable material and a component of a resorbable porous material intended to promote the ingrowth of tissue. U.S. Pat. No. 3,463,158 discloses the use of composites of polyglycolic acid (a resorbable material) and non-absorbable fibre materials for the repair of damaged tissue. U.S. Pat. No. 4,411,027 proposes a coating of a bioresorbable material on the surface of carbon fibre to protect the structure against mechanical damage and to keep fragments in position during the early healing phase. WO 88/06872 discloses a bioresorbable device which structure exhibits longitudinal grooves or channels intended to serve as initial propagation guides for new fibrous tissue.

Devices for the replacement of ligaments have generally failed to show successful long-term results with failure commonly occurring due to synovitis, loosening or implant failure. Following implantation, continuous loading of the device and abrasion against joint tissues causes wear, creep and fatigue of the device until it ultimately fails.

It is an object of the present invention to avoid the problems of the prior art by providing a biocompatible implantable material from which implants for the total or partial replacement of connective tissue can be manufactured. A primary object of the invention is to provide a biocompatible, implantable material from which implants can be manufactured, which are less liable to mechanical failure following implantation into a mammalian patient.

In accordance with a first aspect of the present invention, a biocompatible, implantable material is presented suitable for use in the partial or total replacement or reinforcement of connective tissue, the implantable material comprising a flexible, elongate tape and a plurality of elongate elements, each elongate element being aligned along and independently translatable in the longitudinal direction of the tape.

The independently translatable elements of the present invention mimic the collagen bundles found in connective tissue, such as tendon. This property allows the implantable material to respond to tension, compression and torsion in a way similar to the natural material resulting in a reduced incidence of failure.

Reference herein to any material being "biocompatible" means that the material gives rise to essentially no acute reaction when implanted into a patient.

As used herein, the term "connective tissue" refers to animal tissue in which the extracellular matrix forms the major part, which tissue functions to support and bind other body tissues and parts to one another. Examples of such tissue are ligament, cartilage, bone, meniscus, tendon, skin adipose tissue and areolar tissue.

Reference below to a "support structure" means connective tissue, injured or healthy, to which the implantable material can be attached.

The tape employed in the biocompatible implantable material according to the invention may comprise, woven, non-woven (fibrous material), knitted, braided or crocheted material, foam, sponge, dendritic material, a polymeric film or membrane or a mixture of two or more of these materials. The tape employed in the biocompatible implantable material according to the invention may comprise a porous or a non-porous structure. Preferably, it comprises an at least partially porous structure. This has the advantage of allowing tissue ingrowth, helping to reinforce the structure and avoid mechanical failure. In the event that the tape comprises a porous structure, the percentage open volume of the tape may be in the range 30–99%. The optimum value will depend upon the application and may be a compromise between attaining a high open volume for rapid and efficient penetration of tissue, and good initial mechanical properties, such as tensile or compressive modulus. Typically, the percentage open volume will be in the range 65–90%.

The elongate elements according to the present invention may be disposed on the surface of the tape, within the tape or a mixture of the two. Advantageously, at least some of the elongate elements are disposed within the tape and preferably all of them are disposed within the tape.

Advantageously, each elongate element is maintained spaced apart from the other elongate element or elements. This facilitates independent movement, since there is a lower tendency for the elongate elements to be drawn along by the translational movement of other elongate elements.

The elongate elements themselves may also comprise woven, non-woven (fibrous material), knitted, braided or crocheted material, foam, sponge, dendritic material, a polymeric film or membrane or a mixture of two or more of these materials. The elongate elements may be generally cylindrical, but need not have a circular cross-section: the cross-section may be essentially circular, but may also be rectangular, triangular, or have an irregular shape or may vary along the length of the elongate element. The elongate elements may comprise a porous or a non-porous structure. Preferably, they comprise an at least partially porous structure, since this permits tissue ingrowth into the structure, helping to reinforce the structure and avoid mechanical failure.

In a particularly preferred form, the elongate elements comprise braided yarns. Braided material has the advantage of a favourable load to elongation relationship, i.e. high strength incorporating sufficient elasticity. Single fibres may not satisfy this criterion and may fatigue and break in vivo.

Advantageously, the elongate elements may be selected to model the load to elongation performance of the material it is sought to replace. In the case of an anterior cruciate ligament, then the elongate elements may comprise braided PLA yarns. In order to model the load to elongation performance of the ACL, the PLA braid will preferably have a pick rate in the range 10 and 30 picks/min, though pick-rates outside this range may also be employed, and comprise up to 80 yarns, preferably 4 to 64 yarns. In addition, each braid may comprise up to 200 filaments and advantageously between 30 and 150 filaments. Finally, these filaments may have a diameter up to 30 $\mu$m and will preferably have a diameter in the range 8–20 $\mu$m.

It will be understood that increasing the number of yarns and/or filaments and/or increasing the diameter of either or both increases the strength of the elongate elements, but decreases the open volume for tissue ingrowth. Values of these parameters are selected will optimise strength and open volume.

In a preferred form, the tape employed in the biocompatible, implantable material according to the invention comprises weft strands, spaced apart from one another in the longitudinal direction. According to this form of the invention, there may additionally be warp strands running essentially parallel to the elongate elements. Inclusion of warp strands has the advantage of increasing the spacing between elongate elements, increasing the open volume for tissue ingrowth.

In a particularly preferred form of the first aspect of the present invention, the tape comprises at least two essentially parallel layers of an open mesh, each layer itself comprising warp and weft strands, the elongate elements being disposed between layers of mesh (between the two layers of mesh, if there are only two).

According to this form of the first aspect of the invention, the elongate elements are merely laid between the layers of mesh so that there is no physical connection between the elongate elements and the layers of mesh, thus enabling independent longitudinal translation of each elongate element.

According to this form of the first aspect of the invention, the elongate elements may be kept spaced apart from one another by means of corresponding weft strands from the layer above and the layer below. This may be achieved in a number of ways, but is preferably effected by linking the weft strand from the layer above the elongate element with a corresponding weft strand from the layer below the elongate element at a position between the elongate elements. This linking may be achieved by a number of methods, for example by means of adhesive, by spot-fusing the upper and lower weft strands together or by running a warp strand between the elements to link the upper and lower weft strands. The warp strand used may, for example, be incorporated in the form of a chain stitch or may be woven in. By co-operating in this manner, the weft strands of each layer are also maintained in a spaced apart relationship with respect to one another.

In a further modification of this form of the invention, the elongate elements may be disposed side-by-side. The elongate elements may be spaced a constant distance apart or the distance between successive elongate elements may vary. Preferably, the distance between elongate elements is constant and in the range of up to 30 gauge, more preferably the separation of the elongate elements is in the range 7 to 15 gauge and most preferably it is 10 gauge. The preferred values represent an advantageous balance between high strength and high open volume for tissue ingrowth.

The tape employed in the biocompatible, implantable material according to the invention may comprise bioresorbable or non-bioresorbable material or a mixture of the two.

Reference herein to a material being bioresorbable means that it breaks down over time due to the chemical/biological action of the body and the terms "resorption" and "resorb" are to be interpreted accordingly. Preferably, complete resorption occurs within about 5 years of implantation, more preferably within about 3 years. An advantage of using bioresorbable materials is that further surgery to remove them is not necessary, since they are absorbed back into the body.

A wide range of bioresorbable materials is known, with differing in vivo resorption times. Not only does the resorption time vary according to the material, but the resorption time of a single material itself can also vary significantly with molecular weight. Finally, it can readily be appreciated that by blending and/or copolymerising different bioresorbable materials and/or by modifying the molecular weights of the components, it is possible precisely to tailor the resorption time of the bioresorbable material to the requirement at hand.

With the above in mind, the bioresorbable materials may comprise bioresorbable polymers or copolymers comprising the following monomers or mixtures of polymers and/or copolymers formed thereby: hydroxy acids, particularly lactic acid, glycolic acid; caprolactone; hydroxybutyrate; dioxanone; orthoesters; orthocarbonates; aminocarbonates.

The bioresorbable material may also comprise natural materials such as collagen, cellulose, fibrin, hyaluronic acid, fibronectin, chitosan or mixtures of two or more of these materials. The bioresorbable materials may also comprise devitalised xenograft and/or devitalised allograft.

Preferred bioresorbable materials comprise poly(lactic acid), poly(glycolic acid), polydioxanone, polycaprolactone, polyhydroxybutyrate and poly(trimethylene carbonate) or mixtures thereof.

It is particularly preferred that the biocompatible implantable material comprise poly(lactic acid). This material has the advantage that it has good mechanical strength and does not resorb too quickly, thus allowing its mechanical properties to be retained for a sufficient time for tissue repair to occur at which point the repaired tissue can take over load-bearing functions—reference is made to A. G. A. Coombes and M. C. Meikle, "Resorbable Synthetic Polymers as Replacements for Bone Graft", Clinical Materials 17, (1994), pp 35–67.

Appropriate non-bioresorbable materials include polyesters, particularly aromatic polyesters, such as polyalkylene terephthalates, like polyethylene terephthalate and polybutylene terephthalates; polyamides; polyalkenes such as polyethylene and polypropylene; poly(vinyl fluoride), polytetrafluoroethylene, carbon fibres, silk (natural or synthetic), carbon fibre, glass and mixtures of these materials. An advantage of non-bioresorbable materials is that they essentially retain their initial mechanical properties—i.e. properties such as strength do not reduce over time.

All components of the biocompatible, implantable material according to the invention may comprise the same materials. Alternatively, some components may comprise different materials or each component of the implantable material may comprise a different material from the other components: in the case where the biocompatible, implantable material comprises warp threads, weft threads and elongate elements, each of these three components may comprise a different material. Alternatively, each may comprise the same material, for example poly(lactic acid).

In a further form of the first aspect of the present invention, the biocompatible, implantable material may be loaded with cells. Incorporation of cells may be carried out either before or after implantation, but is preferably carried out prior to implantation.

The cells are generally incorporated by means of a carrier medium. The carrier medium may be a medium, which is retained by the biocompatible, implantable material, for example a gel such as a hydrogel, or one which substantially passes through the biocompatible, implantable material, such that, after seeding, it is substantially no longer present therein—the cells remaining within the implantable material. Examples of this type of carrier medium are cell culture media, like DMEM (Dulbeco's Modified Eagle's Medium containing 10% calcium).

If the carrier medium is a gel, such as a hydrogel, it may be incorporated within and/or on and/or around the biocompatible, implantable material. In one preferred form, the carrier medium is incorporated within the implantable material, since this efficiently utilises the available open volume for cellular growth. More preferably, the carrier medium occupies the entire open volume of the biocompatible, implantable material. Alternatively, the carrier gel may be incorporated by overlaying a confluent/sub-confluent cell layer onto the implantable material. In a further alternative, the biocompatible, implantable material of the present invention may be used to provide mechanical support for other cell-loaded devices, such as DERMAGRAFT™.

Hydrogels which may be used as carrier media according to the invention comprise positively charged, negatively charged and neutral hydrogels which may be saturated or unsaturated. Examples of hydrogels which may be used according to the invention are collagen (particularly Type 1), fibrin, TETRONICS™ and POLOXAMINES™, which are poly(oxyethylene)-poly(oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatised versions of the above, e.g. polyanions, polycations, peptides, polysaccharides, lipids, nucleic acids or blends, block-copolymers or combinations of the above or copolymers of the corresponding monomers; agarose, methylcellulose, hydroxyproylmethylcellulose, xyloglucan, acetan, carrageenan, xanthan gum/locust beangum, gelatine, collagen (particularly Type 1), PLURONICS™, POLOXAMERS™, POLY (N-isopropylacrylmide) and N-isopropylacrylmide copolymers.

The cells with which the biocompatible, implantable material of the invention may be seeded comprise cells which are terminally differentiated or capable of undergoing phenotypic change e.g. stem cells, pluripotent cells and other precursor cells. More specifically, mesenchymal, tenocytes, ligamentous and chondrocytic cells may be seeded in to the implantable material according to the invention. Preferably, the cells used according to the present invention are autologous or allogenic, although xenogenic cells may also be used (but see above regarding problems associated with this type of cell).

The cell-loaded biocompatible, implantable material may be incubated under standard cell culturing techniques known to those in the art. Furthermore, the implantable material may be incubated under mechanical strain, as disclosed in our patent application PCT/GB94/01455, the entire contents of which are incorporated herein by reference.

The biocompatible, implantable material of the present invention may be used for the partial or total replacement of connective tissue such as ligament, cartilage, bone, meniscus, tendon, skin and the like in mammalian organisms. To this end, it must be converted into an implant suitable for implantation into a mammalian patient.

An implant may be generated by cutting the biocompatible, implantable material into lengths. In this case, the implant would be an essentially planar strip of biocompatible, implantable material.

Alternatively, an implant may be generated by superimposing a plurality of strips of biocompatible, implantable material and fixedly attaching them to one another to create a multi-layer implant.

According to a further alternative, an implant may be generated by rolling a strip of the biocompatible, implantable material (i.e. spirally winding it) to form a generally open, cylindrical, tube-like structure. The free end of the biocompatible, implantable material is preferably sealed. Sealing may be achieved by a number of methods, such as by means of an adhesive, by fusion or by width stitching—by pillow stitching, for example.

A tubular implant as above described may, optionally, be received within a porous sleeve. Such a sleeve may be employed to reduce damage due to wear.

The porous sleeve may be manufactured from bioresorbable or non-bioresorbable materials, such as those disclosed above for manufacture of the tape. Preferably, the porous sleeve is manufactured from bioresorbable material.

The material of the sleeve may comprise woven, nonwoven (fibrous material), knitted, braided or crocheted material, foam, sponge, dendritic material, a polymeric film or membrane or a mixture of two or more of these materials.

The structure of the sleeve material is dependent upon the intended application, but will, in general, be designed to achieve the aim of preventing wear damage while, at the same time, allowing tissue ingrowth, nutrient permeation to and waste product diffusion away from the implant. In a preferred embodiment, the material of the sleeve has the same structure as the biocompatible, implantable material comprised within the implant.

The tubular implant, as described above may find application as a ligament or tendon replacement. In this case, the tubular implant will have a diameter sized to be received within a preformed bone tunnel. Such a tunnel usually has a diameter of between 5 to 14 mm and typically a diameter of 9 mm. Thus the diameter of the tubular implant at each end region thereof is typically between 4 to 14 mm e.g. 9 to 11 mm. Alternatively, the tubular implant of the present invention may be used to augment the damaged tendon or ligament to aid normal healing of the tissue.

According to a further alternative, an implant according to the invention may be generated by manufacturing a bundle comprising a plurality of tubes, manufactured as described above, optionally received along their longitudinal axis within a porous sleeve, also as described above. Such an implant may be employed for partial or total replacement of a mammalian ligament or tendon. In such a case, the tubes will be of lower diameter than when a single tube is used for this purpose. In the event that a sleeve is used, as described above, then it is preferably shorter than the tubes such that the end regions of the tubes protrude outwardly therefrom.

For partial or total replacement of a mammalian ligament or tendon, the end regions of the tubular implant (or implant comprising a bundle of lower diameter tubes if this option is used) may be provided with fixation means to secure them within a bone tunnel, for example. The fixation means may, for example, be a cylindrical block of hydroxyapatite or other biocompatible material into which the end regions are fixedly embedded. Other suitable materials include polyesters such as polypropylene fumarate as disclosed in U.S. Pat. No. 4,722,948. Alternative fixation means include staples, anchors, screw/washer combinations, optionally in combination with a "figure-of-eight" eyelet loop or other loop at the end of the device. In one embodiment, the fixation means known as ENDOBUTTON™ is employed.

The implant of the present invention may be used for the total or partial replacement of the rotator cuff in the glenohumeral joint. The rotator cuff comprises four tendons, the supraspinatus, infraspinatus, teres minor and subcapularis. Ruptures to the supraspinatus are the most common problem encountered. For rotator cuff applications, the implant manufactured from the biocompatible, implantable material according to the invention may be shaped in a generally triangular configuration, as shown in EP 0 7 44 165 or in the short or long Y shape as ultilised in the RCR™ device commercially available from Merck Biomaterial, France. Alternatively, if reinforcement is the issue, an implant comprising a strip of biocompatible, implantable material may suffice. Rotator cuff implants according to the present invention may be secured in place by any conventional means known to those skilled in the art, e.g. suturing, suture anchors, bone fixation devices and bone screws.

The implant of the present invention may also be used to partially/totally replace or augment other tissues such as the achilles tendon, medial collateral ligament (MCL), posterior cruciate ligament (PCL), patella tendon, lateral collateral ligament (LCL) and ligaments and tendons of the elbow and hand.

In another example, the biocompatible, implantable material described herein can be used to repair a patellar tendon harvest site. Typically, when the patellar tendon is harvested from a patient, a portion of the tendon (e.g., the middle one third of the tendon) is harvested with patella and tibial bone plugs integrally attached thereto. The use of the harvested patellar tendon for reconstruction of ligaments is considered advantageous because the tissue is derived from the host patient and the implanted tendon readily allows rapid tissue ingrowth. However, studies have shown that after a patellar tendon autograft, the tissue that replaces the harvested patellar tendon often does not have the histological characteristics of a normal patellar tendon. Moreover, even after healing, patients often experience discomfort and pain at the patellar tendon harvest site.

To repair the patellar tendon harvest site, an implant comprising biocompatible, implantable material is implanted into the site following harvesting of the bone-patellar-tendon-bone graft and secured, e.g., by fixing the implant into the site. In one embodiment, the implant comprising biocompatible, implantable material is disposed along the length of the patellar tendon and the implant is secured to the remaining natural patellar tendon, e.g., by suturing opposite sides of the implant to the tendon. In another embodiment, the implant comprising biocompatible, implantable material is secured to the tibia and patella, e.g., by cementing, suturing, stapling or fixing with one or more screws.

In another example, the implant comprising biocompatible, implantable material described herein is used to repair a ruptured or torn Achilles tendon. For example, the implant can be used to repair tears that occur within the Achilles tendon itself, severing the tendon, or the implantable material can be used to repair ruptures, which result from the tendon tearing off of the calcaneus.

For Achilles tendon repair, the implant comprising biocompatible, implantable material may be composed of elements that have load-bearing properties similar to the naturally occurring Achilles tendon and is designed so as to allow new Achilles tendon growth on the implantable material. The implant preferably comprises a bioresorbable material that has the property of resorbing slowly in the body, e.g., PLA. The slow resorption of the implantable material allows retention of the mechanical properties of the implantable material until a time when the newly reconstructed Achilles tendon can take over the load-bearing functions of the implant.

To repair a torn or ruptured achilles tendon, standard surgical methods of identifying and locating the torn tendon can be used. Briefly, a longitudinal incision is made just medial to the Achilles tendon and the severed end(s) of the ruptured tendon identified. Where the Achilles tendon is severed from within, the opposite ends of the implant comprising biocompatible, implantable material are attached to each of the torn tendon ends, e.g., by suturing the first end of the implantable material to the first end of the torn Achilles tendon and suturing the second end of the implant to the second end of the torn Achilles tendon, thereby reattaching the first and second ends. Alternatively, where the Achilles tendon is torn away from the calcaneus, the surgical method includes attaching a first end of the implant to the calcaneus and the second end of the implant to the torn end of the Achilles tendon, e.g., by suturing, thereby reattaching the Achilles tendon to the calcaneus.

In accordance with a second aspect of the present invention there is provided a method for the total or partial replacement of connective tissue in a mammalian patient comprising the step of implanting an implant as hereinbefore described.

Reference is made to the figures of the application:

FIG. 3 illustrates a SEM photograph of a cross-section view of the biocompatible, implantable material of FIGS. 1 and 2; and FIG. 3' is a schematic representation thereof.

FIG. 4b illustrates a photograph taken of the stained cross-sectional view of the centre of the implant of FIG. 4a.

Reference is made to the following working examples of the invention:

EXAMPLE 1

Manufacture of the Biocompatible, Implantable Material

Figure 1:
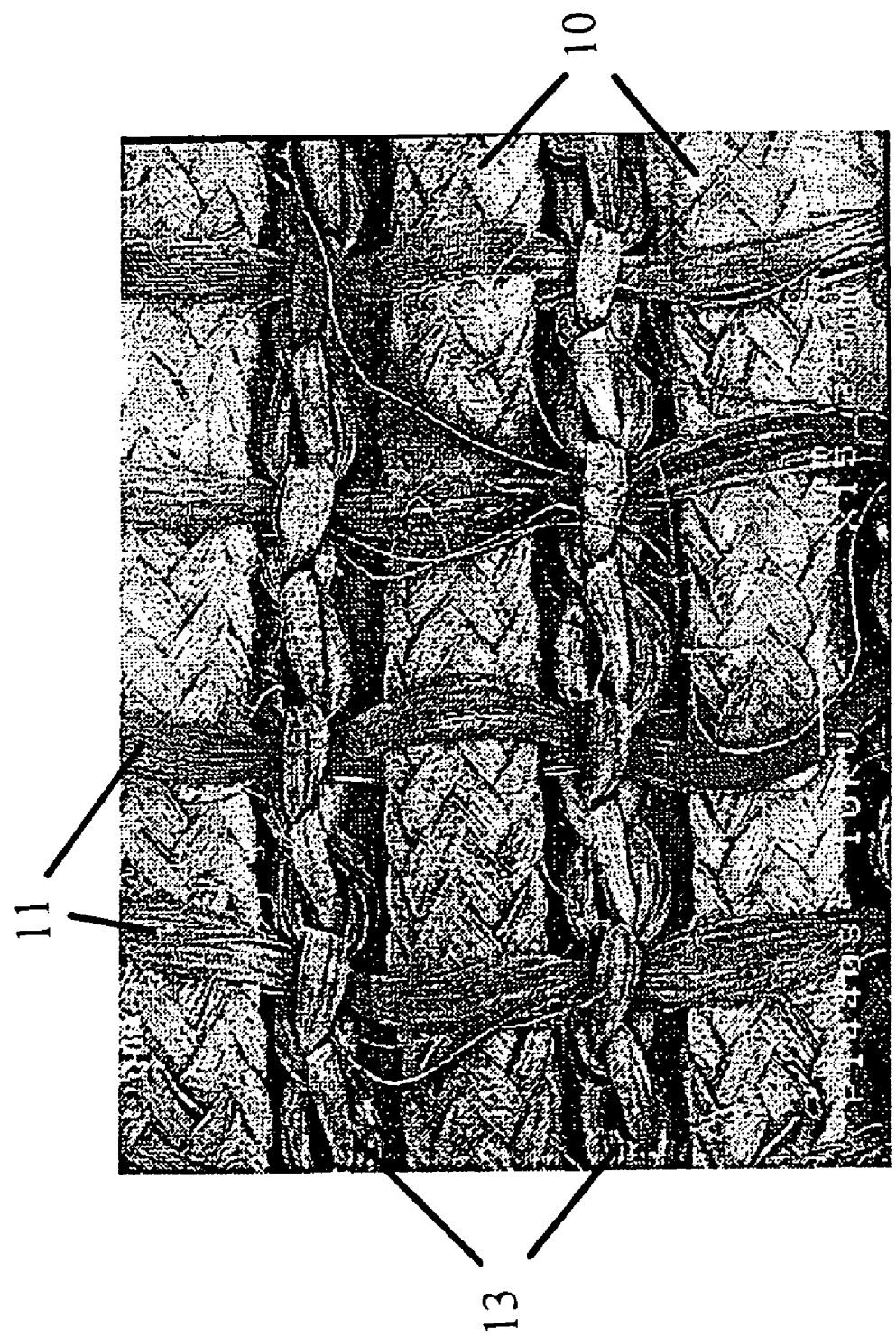
FIG. 1 illustrates a ×15 magnification of scanning electron microscope (SEM) photograph of a biocompatible, implantable material according the invention.
Figure 2:
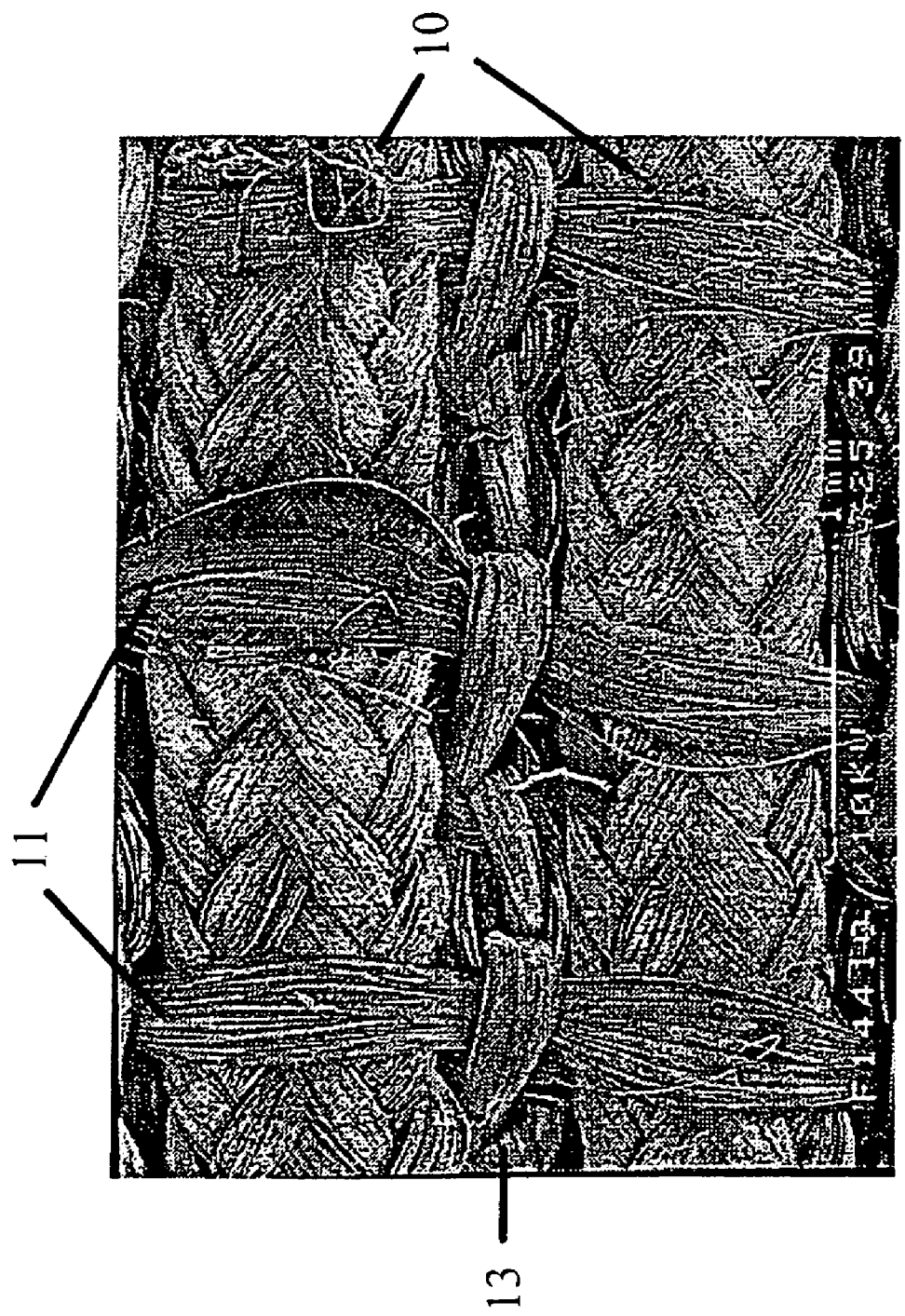
FIG. 2 illustrates a ×25 magnification SEM photograph of a biocompatible, implantable material of FIG. 1

A 10 gauge crochet-knitted biocompatible, implantable material was manufactured using four guide bars. Bar one knits an open chain with poly(lactic acid), PLA, yarn (90 filaments/yarn). Bar two lays in wefts with two yarns covering 11 and 9 needles with PLA yarn. Bar three lays in 18 braids of PLA at 16 ends between the needles without shogging. Bar four is as bar two with the 11 and 9 needles interchanged. All guides are at one thread per guide and bars two and four shog in opposition on every other course. The resulting biocompatible, implantable material, a crochet-knitted warp-knitted material is illustrated in FIGS. 1 and 2. FIGS. 3 and 3' illustrate a cross-sectional views of the material wherein the braids 10 (elongate elements) are aligned alone and independently translatable in the longitudinal direction of the tape as the braids 10 are held between upper and lower wefts (11 and 12 respectively). The wefts 11 and 12 are joined together by strands (13) running between neighbouring braids 10.

Manufacture of the Implant for Ligament Replacement

The biocompatible, implantable material was cut into lengths (180 mm along its longitudinal axis). The crochet threads were removed at positions 15 to 45 mm and 135 to 165 mm from one end of the implant, producing two areas of the biocompatible, implantable material where the wefts did not hold the braids. The material was rolled up along its width to form a tube with the tape lip stitched to the device to prevent unravelling. The sections of the material where the crochet had been removed were divided into two bunches containing an equal number of braids. PLA fibres were then looped around each bunch several times to form two distinguishable eyelets. Each eyelet was then twisted through 180° at its mid-point to form a "figure-of-eight" configuration and placed over two posts spaced at 25 mm apart from one another. PLA fibre was then stitched through the crossover point of the figure-of-eight loops and then tied around the braids. The resulting implant was then sterilised by ethylene oxide.

Preparation of Cell-Seeded Implant

Ovine skin biopsies were treated with dispase solution to remove epidermis. The dermis was chopped into small pieces and cultured in tissue culture media (Gibco, catalogue no. 31885-023) at 37° C. in 5% $CO_2$ incubator until large colonies of fibroblasts were observed. The sterilised implants were then placed in an sterile glass tube and seeded with collagen gel having the fibroblasts dispersed therein at a concentration of approximately $2.18 \times 10^6$ cells for every ml of collagen gel. The implants were placed in an incubator at 37° C. in $CO_2$ overnight.

In Vivo Study

Figure 4A:
FIG. 4a illustrates a photograph taken of the stained cross-sectional view at the tibial bone tunnel/intra-articular space border of an implant, following implantation at the three-week time-point into an adult mammalian model.
Figure 4B:

The cell seeded implant was inserted, into an adult mammalian model, from the lateral aspect of the distal femur, around the caudal aspect of the lateral femoral condyle, through the intercondylar notch and then into the tibial tunnel and anchored to the lateral distal femur by standard orthopaedic screw and washers. The tibial end of the implant was tensioned and anchored with the joint at a standard standing angle (145–155°). The tibial end of the implant was anchored to the medial aspect of the proximal tibia with standard orthopaedic screws and washers with the implant under a tension of approximately 40 N. After three weeks, biochemical analysis of the removed implant indicated a significant increase (approximately 900%) in total collagen levels with corresponding increases in DNA and GAG. Histological results are illustrated in FIGS. 4a and 4b. In FIG. 4a, the implant as situated in the tibial tunnel shows an infiltration of cells and significant staining of a collagenous matrix. Both osteoclastic and osteoblastic activity indicated the resorption and subsequent production of new bone in the surrounding bone tunnel. In FIG. 4b, the stained device showed high levels of collagen and fibroblastic infiltration. The implant had not failed and did not show significant signs of wear, creep or fatigue.

EXAMPLE 2

Rotator Cuff Repair

Implants were generated by cutting biocompatible, implantable material, manufactured as in Example 1, into 20×15 mm lengths (of 1 mm thickness).

Ten matched pairs of fresh shoulders from Merino sheep were dissected to expose the infraspinatus tendon and its insertion. The tendon was carefully detached from its insertion using sharp dissection. The insertion site was measured (average 19.0×13.3 mm). Using an 8 mm square template, four MITEK GII™ suture anchors were used to reattach the infraspinatus tendon using simple stitches #2 ETHIBOND™. In half the samples, the repair was reinforced with an implant, as defined above, placed on the top of the tendon. Sutures were passed through the tendon and implant using standard simple suturing technique. A bone trough 4×15 mm was prepared using a rongeur in the juxta-articular portion of the greater tuberosity. Three #5 ETHIBOND™ sutures were then passed through the trough and through two drill-holes 5 mm apart placed 10 mm distal to the tip of the greater tuberosity. In half of the matched specimens the sutures were reinforced by passage through the scaffold. The ends were tied to form a loop 10 cm long. The samples were then mechanically tested. The humerus was securely fixed to a baseplate and the free end of the tendon or suture loop was attached to a specially designed clamp. Testing to failure at an extension rate of 500 mm/per minute on a SHIMAZU™ mechanical testing machine with a 5kN load cell. The pull was adjusted to be 90 degrees relative to the long axis of the humerus, duplicating the anatomic pull of the tendon with the limb at rest. Specimens were kept moist with saline. Statistical comparisons were performed with two-tailed Student t tests.

The mean ultimate strength of suture anchor rotator cuff repairs augmented with the scaffold (167.3±53.9 N) was significantly greater (p<0.008) than that of the non-augmented fixation (133.2±38.2). The mode of failure was the tendon pulling out from the sutures along fibre orientation. In the reinforced repairs, the scaffold remained in place and intact while the tendon pulled out underneath. The addition of the poly(lactic acid) over the bone bride significantly increased (p<0.0001) the ultimate strength of the fixation from 374.6±117.6N to 480.9±89.2.

The scaffold significantly increased the strength of rotator cuff repair using suture anchors or bone bridge by 1.25 times compared to the non-reinforced repair.

EXAMPLE 3

Figure 5:
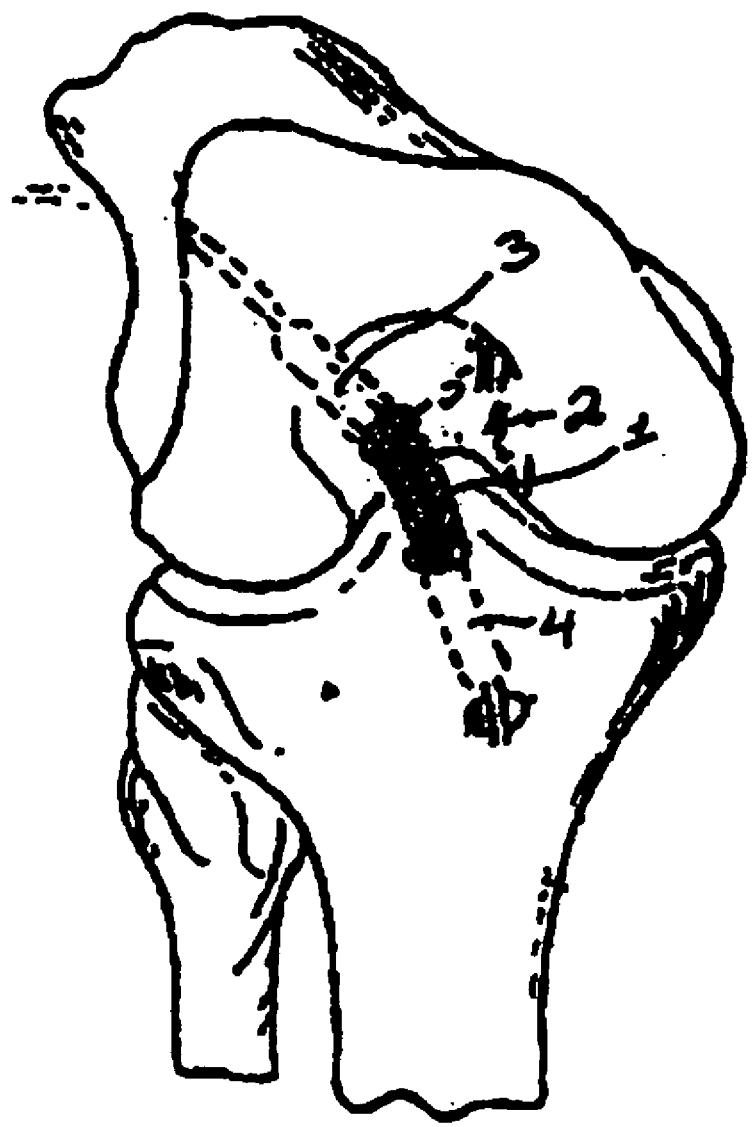
FIG. 5 illustrates a knee joint in which an implant comprising biocompatible implantable material has been implanted during an anterior cruciate ligament (ACL) reconstruction procedure.

Use of an Implant Comprising the Biocompatible. Implantable Material to Repair the ACL Implants comprising the biocompatible, implantable material described herein may be used for reconstructing a torn anterior cruciate ligament (ACL). Referring to FIG. 5, a knee joint is shown in which an implant comprising biocompatible, implantable material 1 has been implanted during an ACL reconstruction procedure. For ACL reconstruction, the implant comprising biocompatible, implantable material 1 is composed of elements that have load-bearing properties similar to the naturally occurring ACL. Biocompatible, implantable material 1 for an ACL repair is designed to be porous so as to allow new ACL tissue growth on implantable material 1. It is important that the porosity does not collapse or decrease significantly when implantable material 1 is extended longitudinally.

The biocompatible, implantable material 1 is preferably composed of the bioresorbable material PLA, which has two key features: PLA resorbs slowly, and it has load-bearing properties similar to the naturally occurring ACL. The slow resorption of implantable material 1 is important so as to allow retention of the mechanical properties of implantable material 1 until a time when the newly reconstructed ACL can take over the load-bearing functions of implantable material 1.

Prior to implanting implantable material 1, the surgeon removes the torn ACL stump from the intercondylar notch and clears the ligament. A notchplasty procedure is preferably performed to expand the intercondylar notch 2 of the femur (an example of such a notchplasty procedure is described in U.S. Pat. No. 5,139,520, the contents of which are incorporated herein by reference). A femoral tunnel 3 for receiving one end of the implant comprising biocompatible, implantable material 1 and a tibial tunnel 4 for receiving the other end of implantable material 1 are drilled. The two tunnels should be formed so that they enter the joint at the proper anatomic attachment points. These points are preferably on the knee joint surfaces where the original ACL was attached. The procedure for providing the femoral tunnel 3 and tibial tunnel 4 is described in greater detail in U.S. Pat. No. 5,306,301, the contents of which are incorporated herein by reference.

The implantable material 1 is inserted through the femoral tunnel 3 and exits an opening in the femur 5. The femoral end of the implantable material 1 is attached to the femur by any of a number of different procedures known in the art, e.g., cementing, suturing, stapling, or fixing with a screw. The tibial end of implantable material 1 is then passed from the joint space into the tibial tunnel 4. The tibial end of the implantable material 1 is tensioned and attached within the tibial tunnel, e.g., by cementing, suturing, stapling, or fixing with a screw. Once the implant comprising biocompatible, implantable material 1 is secured in place in the tibia, it is viewed arthroscopically and is assessed for taughtness. The knee is also moved through its normal range of motion to assure that impingement of implantable material 1 does not occur. Following implantation to the satisfaction of the surgeon, excess length of implantable material 1, if necessary, is removed from the tibia.

What is claimed is:

1. Biocompatible, implantable material suitable for use in the partial or total replacement or reinforcement of connective tissue, the implantable material comprising:
   a flexible, elongate tape, said tape being generally planar, having a longitudinal direction, and including
   (a) a series of parallel warp strands extending longitudinally, and
   (b) a series of parallel weft strands which cross the warp strands and which have first interconnections with the warp strands to locate the weft strands in place spaced relative to one another;
   a plurality of elongate elements, each elongate element
   (a) having a property which mimics the connective tissue being replaced or reinforced, the property of the elongate elements being different from a corresponding property of the warp strands, and
   (b) being aligned between respective adjacent parallel warp strands; and
   second interconnections between said weft strands and each of said plurality of elongate elements, said second interconnections holding each elongate element to the tape so as to be
   (a) in an orientation parallel to one another and to the longitudinal direction of the tape,
   (b) separated from one another in the plane of the tape, and
   (c) independently translatable in the longitudinal direction relative to one another and to the tape.

2. Biocompatible, implantable material according to claim 1, wherein the tape comprises, woven, non-woven, knitted, braided or crocheted material, foam, sponge, dendritic material, a polymeric film or membrane or a mixture of two or more of these materials.

3. Biocompatible, implantable material according to claim 1, wherein the elongate elements comprise woven, non-woven, knitted, braided or crocheted material, foam, sponge, dendritic material, a polymeric film or membrane or a mixture of two or more of these materials.

4. Biocompatible, implantable material according to claim 1, wherein the tape comprises bioresorbable material, non-bioresorbable material or a mixture of the two.

5. Biocompatible, implantable material according to claim 4, wherein the bioresorbable material comprises poly (lactic acid), poly(glycolic acid), polydioxanone, polycaprolactone, polyhydroxybutyrate, poly(trimethylene carbonate) or mixtures of these materials.

6. Biocompatible, implantable material according to claim 4, wherein the non-bioresorbable material comprises polyester, polyamide, polyalkene, poly(vinyl fluoride), polytetrafluoroethylene, carbon fibre, silk, carbon fibre, glass or mixtures of these materials.

7. Biocompatible, implantable material according to claim 1, wherein the elongate elements comprises bioresorbable material, non-bioresorbable material or a mixture of the two.

8. Biocompatible, implantable material according to claim 1 additionally comprising cells.

9. Biocompatible, implantable material according to claim 8, wherein the cells are mesenchymal cells, tenocytes, ligamentous calls, chondrocytic cells or a mixture of these.

10. Biocompatible, implantable material according to claim 1, wherein the implant also comprises hydrogel.

11. Biocompatible, implantable material according to claim 1, wherein the elongate elements comprise braided yarns.

12. Implant comprising the biocompatible material according to claim 1.

13. Implant according to claim 12, wherein said tape is flat which flat tape is then spirally wound into a tube of biocompatible, implantable material.

14. Method for the total or partial replacement of connective tissue in a mammalian patient comprising the step of implanting an implant as defined in claim 12.

15. Biocompatible, implantable material according to claim 1:
   wherein the series of parallel weft strands includes respective upper and lower weft strands disposed on opposite sides of the plane of the tape; and
   wherein said second interconnections are formed by crossing portions of said upper and lower weft strands engaging said elongate elements.

16. Biocompatible, implantable material according to claim 15,
   wherein the upper and lower weft strands are perpendicular to the warp strands; and wherein the first interconnections are formed by passing the upper and lower weft strands through the warp strands.

17. Biocompatible, implantable material according to claim 16, wherein each elongate element is maintained spaced apart from the adjacent warp strands by the upper and lower weft strands.

18. A method of supporting tissue growth at a selected site in a body, comprising:
providing a biocompatible, implantable material comprising
a flexible, elongate tape which is generally planar, which has a longitudinal direction, and which includes
(a) a series of parallel warn strands extending longitudinally, and
(b) a series of parallel weft strands which cross the warp strands and which have first interconnections with the warp strands to locate the weft strands in place spaced relative to one another;
a plurality of elongate elements, each elongate element
(a) having a property which mimics the tissue being grown, the property of the elongate elements being different from a corresponding property of the warp strands, and
(b) being aligned between respective adjacent parallel warp strands; and
second interconnections between the weft strands and each of the plurality of elongate elements, the second interconnections holding each elongate element to the tape so as to be
(a) in an orientation parallel to one another and to the longitudinal direction of the tape,
(b) separated from one another in the plane of the tape, and
(c) independently translatable in the longitudinal direction relative to one another and to the tape; and
implanting the implantable material at the selected site.

19. The method of claim 18 wherein the implanting includes attaching the implantable material to a tissue at the selected site.

20. The method of claim 19 wherein the tissue to which the implantable material is attached is a connective tissue.

21. The method of claim 20 wherein the connective tissue is a ligament, tendon or muscle.

22. The method of claim 19 wherein the attaching is performed by cementing the implantable material to the tissue.

23. The method of claim 19 wherein the attaching is performed by suturing the implantable material to the tissue.

24. The method of claim 19 wherein the attaching is performed by fixing the implantable material to the tissue with at least one screw.

25. The method of claim 18 wherein the implanting includes attaching a first portion of the implantable material to a first support structure and attaching a second portion of the implantable material to a second support structure, such that the implantable material connects the first support structure to the second support structure.

26. The method of claim 25 wherein the first and second support structures are a tibia and a femur, said attaching further comprising attaching the first and second portions of the implantable material to regions of the tibia and femur, respectively, proximate attachment regions of a natural cruciate ligament.

27. The method of claim 25 wherein the first and second support structures are a tibia and a femur, said attaching further comprising attaching the first and second portions of the implantable material to regions of the tibia and femur, respectively, proximate attachment sites of a natural collateral ligament.

28. The method of claim 25 wherein the first and second support structures are a humerous and a rotator cuff muscle, said attaching comprising attaching the first and second portions of the implantable material to regions of the humerous and the rotator cuff muscle, respectively, thereby reattaching the rotator cuff muscle to the humerous.

29. The method of claim 25 wherein the first support structure is a first portion of a torn Achilles tendon and the second support structure is a second portion of the torn Achilles tendon, said attaching further comprising attaching the first portion of the implantable material to the first portion of the torn Achilles tendon and the second portion of the implantable material to the second portion of the torn Achilles tendon, thereby reattaching the portions.

30. The method of claim 25 wherein the first and second support structures are a tibia and a patella, said attaching further comprising attaching the first and second portions of the implantable material to regions of the tibia and patella, respectively, proximate attachment sites of a natural patellar tendon.

31. A method of supporting growth of a knee ligament, comprising:
providing a biocompatible, implantable material comprising
a flexible, elongate tape which is generally planar, which has a longitudinal direction, and which includes
(a) a series of parallel warp strands extending longitudinally, and
(b) a series of parallel weft strands which cross the warn strands and which have first interconnections with the warp strands to locate the weft strands in place spaced relative to one another:
a plurality of elongate elements, each elongate element
(a) having a property which mimics the ligament being grown, the property of the elongate elements being different from a corresponding property of the warp strands, and
(b) being aligned between respective adjacent parallel warp strands; and
second interconnections between the weft strands and each of the plurality of elongate elements, the second interconnections holding each elongate element to the tape so as to be
(a) in an orientation parallel to one another and to the longitudinal direction of the tape
(b) separated from one another in the plane of the tape, and
(c) independently translatable in the longitudinal direction relative to one another and to the tape;
attaching a first portion of the implantable material to a first support structure of the knee; and
attaching a second portion of the implantable material to a second support structure of the knee.

32. The method of claim 31 wherein the first and second support structures are a tibia and a femur, said attaching comprising attaching the first and second portions of the implantable material to regions of the tibia and femur, respectively, proximate attachment regions of a natural cruciate ligament.

33. The method of claim 31 wherein the first and second support structures are a tibia and a femur, said attaching comprising attaching the first and second portions of the implantable material to regions of the tibia and femur, respectively, proximate attachment regions of a natural collateral ligament.

34. A method of supporting growth of a rotator cuff, comprising:
   providing a biocompatible, implantable material comprising
      a flexible, elongate tape which is generally planar, which has a longitudinal direction, and which includes
         (a) a series of parallel warp strands extending longitudinally, and
         (b) a series of parallel weft strands which cross the warp strands and which have first interconnections with the warn strands to locate the weft strands in place spaced relative to one another;
      a plurality of elongate elements, each elongate element
         (a) having a property which mimics the tissue being grown, the property of the elongate elements being different from a corresponding property of the warp strands, and
         (b) being aligned between respective adjacent parallel warp strands; and
      second interconnections between the weft strands and each of the plurality of elongate elements, the second interconnections holding each elongate element to the tape so as to be
         (a) in an orientation parallel to one another and to the longitudinal direction of the tape,
         (b) separated from one another in the plane of the tape, and
         (c) independently translatable in the longitudinal direction relative to one another and to the tape; and
   attaching a first portion of the implantable material to a first support structure of the shoulder; and
   attaching a second portion of the implantable material to a second support structure of the shoulder.

35. The method of claim 34 wherein the first and second support structures are a humerous and a rotator cuff muscle, said attaching comprising attaching the first and second portions of the implantable material to regions of the humerous and rotator cuff muscle, respectively, thereby reattaching the rotator cuff muscle to the humerous.

36. A method of supporting growth of an Achilles tendon, comprising:
   providing a biocompatible, implantable material comprising
      a flexible, elongate tape which is generally planar, which has a longitudinal direction, and which includes
         (a) a series of parallel warp strands extending longitudinally, and
         (b) a series of parallel weft strands which cross the warp strands and which have first interconnections with the warp strands to locate the weft strands in place spaced relative to one another;
      a plurality of elongate elements, each elongate element
         (a) having a property which mimics the tissue being grown, the property of the elongate elements being different from a corresponding property of the warp strands, and
         (b) being aligned between respective adjacent parallel warn strands; and
      second interconnections between the weft strands and each of the plurality of elongate elements, the second interconnections holding each elongate element to the tape so as to be
         (a) in an orientation parallel to one another and to the longitudinal direction of the tape,
         (b) separated from one another in the plane of the tape, and
         (c) independently translatable in the longitudinal direction relative to one another and to the tape; and
   attaching a first portion of the implantable material to a first support structure of an ankle; and
   attaching a second portion of the implantable material to a second support structure of the ankle.

37. The method of claim 36 wherein the first support structure is a first portion of a torn Achilles tendon and the second support structure is a second portion of the torn Achilles tendon, said attaching further comprising attaching the first portion of the implantable material to the first portion of the torn Achilles tendon and the second portion of the implantable material to the second portion of the torn Achilles tendon, thereby reattaching the portions.

38. A method of treating a tissue harvest site, comprising:
   providing a biocompatible, implantable material comprising
      a flexible, elongate tape which is generally planar, which has a longitudinal direction, and which includes
         (a) a series of parallel warn strands extending longitudinally, and
         (b) a series of parallel weft strands which cross the warp strands and which have first interconnections with the warp strands to locate the weft strands in place spaced relative to one another;
      a plurality of elongate elements, each elongate element
         (a) having a property which mimics the tissue being treated, the property of the elongate elements being different from a corresponding property of the warp strands, and
         (b) being aligned between respective adjacent parallel warp strands; and
      second interconnections between the weft strands and each of the plurality of elongate elements, the second interconnections holding each elongate element to the tape so as to be
         (a) in an orientation parallel to one another and to the longitudinal direction of the tape,
         (b) separated from one another in the plane of the tape, and
         (c) independently translatable in the longitudinal direction relative to one another and to the tape; and
   implanting the implantable material at the harvest site.

39. The method of claim 38 wherein the tissue harvest site is at a patellar tendon.

40. The method of claim 38 wherein the tissue harvest site is at a semitendinosus.

* * * * *